(12) United States Patent
Godal et al.

(10) Patent No.: US 8,546,447 B2
(45) Date of Patent: *Oct. 1, 2013

(54) TREATMENT OF ACNE USING DERIVATIVES OF 5-AMINOLEVULINIC ACID

(71) Applicant: Photocure ASA, Oslo (NO)

(72) Inventors: Aslak Godal, Oslo (NO); Jo Klaveness, Oslo (NO); Hilde Morris, Oslo (NO)

(73) Assignee: Photocure ASA, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/673,704

(22) Filed: Nov. 9, 2012

(65) Prior Publication Data

US 2013/0066256 A1 Mar. 14, 2013

Related U.S. Application Data

(63) Continuation of application No. 11/667,504, filed as application No. PCT/GB2005/004253 on Nov. 4, 2005.

(30) Foreign Application Priority Data

Nov. 10, 2004 (GB) .................................. 0424833.2

(51) Int. Cl.
*A01N 37/00* (2006.01)
*A61K 31/21* (2006.01)
*C07C 69/74* (2006.01)
*C07C 229/00* (2006.01)
*C07C 69/66* (2006.01)

(52) U.S. Cl.
USPC ................ 514/506; 560/1; 560/155; 560/174

(58) Field of Classification Search
USPC .............................. 514/506; 560/1, 155, 174
See application file for complete search history.

(56) References Cited

U.S. PATENT DOCUMENTS

| | | | |
|---|---|---|---|
| 5,079,262 A | 1/1992 | Kennedy et al. | |
| 5,234,940 A | 8/1993 | Kennedy et al. | |
| 5,422,093 A | 6/1995 | Kennedy et al. | |
| 5,713,845 A | 2/1998 | Tankovich | |
| 5,955,490 A | 9/1999 | Kennedy et al. | |
| 6,034,267 A | 3/2000 | Gierskcky et al. | |
| 6,183,773 B1 | 2/2001 | Anderson | |
| 6,600,951 B1 | 7/2003 | Anderson | |
| 6,710,066 B2 | 3/2004 | Kennedy et al. | |
| 6,897,238 B2 | 5/2005 | Anderson | |
| 2003/0125388 A1 | 7/2003 | Gander et al. | |
| 2004/0048842 A1 | 3/2004 | McMillan | |
| 2005/0209330 A1 | 9/2005 | Kreindel | |
| 2005/0209331 A1 | 9/2005 | Kreindel | |

FOREIGN PATENT DOCUMENTS

| | | |
|---|---|---|
| EP | 0995448 A1 | 4/2000 |
| WO | 93/20810 A3 | 11/1993 |
| WO | 94/06424 A1 | 3/1994 |
| WO | 96/28412 A1 | 9/1996 |
| WO | 02/10120 A1 | 2/2002 |
| WO | 02/13788 A1 | 2/2002 |
| WO | 01/55092 B1 | 3/2002 |
| WO | 03/011265 A3 | 4/2003 |
| WO | 03/039597 A1 | 5/2003 |
| WO | 2005/092838 A1 | 10/2005 |

OTHER PUBLICATIONS

Morton et al. British Journal of Dermatology 2002 (146) 552-567.*
Gold et al. Dermatological Surgery 2004 (30) 1077-1084.*
Itoh et al. British Journal of Dermatology 2001 (144) 575-579.*
Itoh et al. Archives Dermatology 2000 (136) 1093-1095.*
Hongchara et al. The Journal of Investigative Dermatology 2000 (115) 183-192.*
Gold; Lasers in Surgery and Medicine 2003 (32) 46.*
Alexiades-Armenakas; Lasers in Surgery and Medicine 2003 (32) 46.*
Ashkenazi et al., "Eradication of *Propionibacterium acnes* by its endogenic prophyrins after illumination with high intensity blue light," FEMS Immunology and Medical Microbiology, vol. 35, 2003, pp. 17-24.
Baxter et al., "Evidence for Specific Lead-?-aminolevulinate Complex Formation by Carbon-13 Nuclear Magnetic Resonance Spectroscopy," Toxicology and Applied Pharmacology 47, pp. 477-482 (1979).
Douglas, H.D. and Gunter, S.E., J. Bacteriol., 1946, vol. 52, pp. 15-23.
Drugs of the Future, 1997, vol. 22, Part 1, pp. 11-17.
Futsaether et al., Can. J. Microbiol. 39(2): 180-186 (1993).
Goodsell, M.E. et al., Curr. Microbiol., 1991, vol. 22, pp. 225-230.
Itoh Y, et al., "Photodynamic Therapy of *Acne vulgaris* with Topical Delta-Aminolaevulinic Acid and Incoherent Light on Japanese Patients," British Journal of Dermatology, vol. 144, 2001, pp. 575-579.
Johnson, J.L., and Cummins, C.S., J. Bacteriol. 1972, vol. 109, pp. 1047-1066.
Kennedy et al., J. Clin. Laser Med. Surg. 14: 289-304 (1996).
Kloek et al. (Photochemistry adn Photobiology, vol. 64, No. 6, pp. 994-1000; 1996).
Merck Manual reference ([Retrieved on 2009-80-16] from the Internet: URL: http://www.merck.com/mmhe/sec18/ch204a.html?qt=acne%vulgaris&alo=sh).
Merck Manuals Online Medical Dictionary (Retrieved on Aug. 16, 2009 from the Internet: URL:http//www.merck.com/mmhe/sec18ch204a.html?qt=prevent%20acne&alt=sh).
Peng et al., Journal of Photochemistry and Photobiology B: Biology, vol. 34, pp. 95-96; 1996).
Pollock, B. et al., "Topical Aminolaevulinic Acid-Photodynamic Therapy for the Treatment of *Acne vulgaris*: A Study of Clinical Efficacy and Mechanism of Action," British Journal of Dermatology, vol. 151, No. 3, Sep. 2004.
Skerman, V.B. et al., Int. J. Syst. Bacteriol. 1980, vol. 30, pp. 225-420.
Stoughton et al., Drug Dpv. Ind. Pharm., 1983, vol. 9, pp. 725-744.
The Journal of Investigative Dermatology, vol. 115(2), Aug. 2000, pp. 183-192.

(Continued)

*Primary Examiner* — Jeffrey S. Lundgren
*Assistant Examiner* — Michael Schmitt
(74) *Attorney, Agent, or Firm* — Kenyon and Kenyon LLP

(57) ABSTRACT

The invention provides use of a photosensitiser, which is a derivative (e.g., an ester) of 5-aminolevulinic acid (5-ALA) or a pharmaceutically acceptable salt thereof, in the manufacture of a medicament for use in the prevention or treatment of acne.

21 Claims, 11 Drawing Sheets

(56) References Cited

OTHER PUBLICATIONS

Van Den Bergh, Chemistry in Britain, May 1986, pp. 430-439.
Wang, R.F., Appl. Environ. Microbiol., 1996, vol. 62, pp. 1242-1247.
Wiegell et al., "Photodynamic therapy of *Acne vulgaris* using 5-aminolevulinic acid versus methyl aminolevulinate", American Academy of Dermatology, Inc., pp. 647-651, 2006.
Woodford et al., J. Toxicol., Tut. & Ocular Toxicology, 1986, vol. 5, pp. 167-177.
Wu, Jie, "The status quo and development of a medicament for the treatment of acne," Gazette of Youjiang Nationalities Medical School 3: 464-466 (2001).
Zierot, C.H. et al., Int. J. Syst. Bacteriol, 1968, vol. 18, pp. 33-47.

* cited by examiner

TREATMENT OF ACNE USING DERIVATIVES OF 5-AMINOLEVULINIC ACID

This application is a continuation application of U.S. patent application Ser. No. 11/667,504, filed Nov. 9, 2007, which is the U.S. national phase of PCT Application No. PCT/GB2005/004253, filed Nov. 4, 2005, which claims priority to British Patent Application No. 0424833.2, filed Nov. 10, 2004, the entire contents of which are incorporated herein.

This invention relates to the treatment of acne, and in particular to the use of derivatives of 5-aminolevulinic acid (5-ALA) in a method of treating acne, e.g. acne vulgaris. Most particularly, the invention relates to the use of 5-ALA esters for the treatment of such conditions.

Acne is one of the most common skin disorders throughout the world. Although particularly prevalent during puberty, it may continue for many years. It affects approximately 83-95% of 16 year olds of both sexes in the UK and about 20% of sufferers seek help from a clinician. It can in some cases cause permanent scarring and is often the source of considerable emotional distress.

In its milder forms, acne is a superficial disorder which is accompanied by slight, spotty irritations. However, in the more inflammatory types of acne, bacterial invasion of or about the pilosebaceous follicles occurs resulting in the formation of pustules, infected cysts, etc. These lesions may become extensive and often leave permanent, disfiguring scars.

The precise cause of acne is not fully understood although obstruction of the pilosebaceous canal is believed to be a primary factor. This may be caused by overproduction of sebum, increased turnover of epithelial cells and/or the proliferation of bacteria (e.g. *Propionibacterium acnes*). It is believed, for example, that excess sebum production and increased turnover of epithelial cells may cause clogging or blockage of the skin's pores and lead to formation of comedones (blackheads) and whiteheads. If certain bacteria are present in combination with these factors, inflammatory lesions such papules, pustules and cysts may form.

Blackheads, whiteheads, papules, pustules and cysts are commonly referred to as "spots". Each type of spot may be present to a different degree in any acne sufferer and most commonly a range of different types are found. Spots generally occur on the face and back, especially the facial skin areas (e.g. on the chin, nose and forehead) where sebaceous glands are the largest, most prevalent and most active.

Established treatments of acne are designed to prevent the formation of new lesions and to facilitate the healing of existing lesions. Conventional treatments include, for example, the systemic and topical administration of antibiotics which aim to reduce the bacterial population of the pilosebaceous follicles and the topical application of peroxides, e.g. benzoyl peroxide, which are both anti-bacterial and mildly comedolytic. Vitamin A analogs, such as retinoids, are comedolytic and have also been used with a some degree of success in topical acne treatment compositions.

There are, however, problems emerging with such conventional treatments. For instance, peroxides such as benzoyl peroxide are often unstable and therefore have limited shelf-life. Their efficacy also tends to decrease over time. Antibiotic resistance of *Proprionibacterium acnes* is also increasing and this severely reduces efficacy. Retinoid drugs (e.g. isotretinoin), though effective, often cause unpleasant, and sometimes severe, side-effects and contraindications often limit their acceptability and use. There is therefore a need for the development of alternative treatments for acne.

One method which has recently been proposed for the treatment of acne is photodynamic therapy (PDT) using photosensitizing agents. Photodynamic therapy (PDT) is a relatively new technique which has been used in the treatment of various abnormalities or disorders of the skin or other epithelial organs or mucosa, especially cancer or pre-cancerous lesions, as well as certain non-malignant lesions such as psoriasis. PDT involves the administration of photosensitizing agents followed by exposure to photoactivating light in order to activate the photosensitizing agents and convert them into cytotoxic form resulting in the destruction of cells and thus treatment of the disease. Several photosensitizing agents are known and described in the literature, for example various porphyrins psoralens, chlorins, phthalocyanines, as well as 5-aminolevulinic acid (5-ALA) and certain derivatives thereof, e.g. 5-ALA esters.

Although PDT has focused primarily on treatment of cancer and pre-cancerous stages, there are some reports relating to the use of PDT in treating acne. Such methods, however, have enjoyed only limited success. For example, Itoh, Y. et al. (*Brit. J. Dermatology*, 2001, 14 575-579) and Hongcharau, W. et al. (*J. Invest. Dermatology*, 2000, 115 183-192) both describe trials on PDT treatment of acne using 5-ALA as a photosensitiser. Both studies conclude that ALA-PDT may be effective for treatment of acne but note that significant adverse effects are associated with the treatment. These include discomfort, burning, itching and stinging during the irradiation, oedematous erythema and epidermal exfoliation shortly after PDT, and prolonged irritation and hypersensitivity to physical stimulation for up to 10 days following the treatment. Pigmentation was also reported in a number of cases and patients' skin took up to a month to return to normal.

An additional problem associated with the use of 5-ALA in therapy (e.g. in PDT) is that it is extremely unstable and has a tendency to undergo a plethora of decomposition reactions. As a result of its instability, 5-ALA is typically presented as an acidic composition (it is most stable below pH 5) but this in turn further reduces its acceptability as a therapeutic substance. 5-ALA also has a relatively low bioavailability which means it often has to be used in high doses, thus exacerbating the problems associated with the acidity of many 5-ALA compositions.

A need still therefore exists for alternative methods to treat and/or prevent acne. Despite the various problems highlighted in the literature in relation to the treatment of acne using PDT with 5-ALA, we have now surprisingly found that derivatives of 5-ALA (e.g. 5-ALA esters, especially optionally substituted benzyl ALA esters) can effectively be used in photodynamic treatment of acne.

Thus, viewed from one aspect the invention provides the use of a photosensitiser which is a derivative (e.g. an ester) of 5-aminolevulinic acid (5-ALA), or a pharmaceutically acceptable salt thereof, in the manufacture of a medicament for use in the prevention or treatment of acne.

In a further aspect the invention provides a method for treating or preventing acne, said method comprising administering (e.g. topically applying) to an area of skin (e.g. an affected area of skin) on a body, a photosensitiser which is a derivative (e.g. an ester) of 5-aminolevulinic acid (5-ALA), or a pharmaceutically acceptable salt thereof, and photoactivating said photosensitiser.

In particular, the invention provides a method of treating or preventing acne, said method comprising the steps of:

(a) administering (e.g. topically applying) to an area of skin (e.g. an affected area of skin) on said body, a photosensitiser which is a derivative (e.g. an ester) of 5-aminolevulinic acid (5-ALA), or a pharmaceutically acceptable salt thereof;

(b) optionally waiting for a time period necessary for the photosensitiser to achieve an effective tissue concentration at the desired (e.g. affected) site; and (c) photoactivating the photosensitiser at the desired (e.g. affected) site.

The use of derivatives of 5-ALA (5-amino-4-oxo-pentanoic acid, otherwise known as 5-aminolevulinic acid) in PDT is well known in the scientific and patent literature (see, for example, J. C. Kennedy et al., J. Clin. Laser Med. Surg. (1996) 14: 289-304, U.S. Pat. No. 5,079,262, U.S. Pat. No. 5,211,938, U.S. Pat. No. 5,234,940, U.S. Pat. No. 5,422,093, U.S. Pat. No. 6,034,267, WO91/01727 and WO96/28412, the contents of which are incorporated herein by reference). All such derivatives of 5-ALA and their pharmaceutically acceptable salts are suitable for use in the methods herein described.

The 5-ALA derivatives useful in accordance with the invention may be any derivative of 5-ALA capable of forming protoporphyrin IX (PpIX) or any other photosensitiser (e.g. a PpIX derivative) in vivo. Typically, such derivatives will be a precursor of PpIX or of a PpIX derivative (e.g. a PpIX ester) in the biosynthetic pathway for haem and which are therefore capable of inducing an accumulation of PpIX at the site of the acne following administration in vivo. Suitable precursors of PpIX or PpIX derivatives include 5-ALA prodrugs which might be able to form 5-ALA in vivo as an intermediate in the biosynthesis of PpIX or which may be converted (e.g. enzymatically) to porphyrins without forming 5-ALA as an intermediate. 5-ALA esters are among the preferred compounds for use in the methods herein described.

Esters of 5-aminolevulinic acid and N-substituted derivatives thereof are preferred photosensitisers for use in the invention. Those compounds in which the 5-amino group is unsubstituted (i.e. the ALA esters) are particularly preferred. Such compounds are generally known and described in the literature (see, for example, WO96/28412 and WO02/10120 to PhotoCure ASA, the contents of which are incorporated herein by reference).

Esters of 5-aminolevulinic acid with substituted or unsubstituted, preferably substituted, alkanols, i.e. alkyl esters or, more preferably, substituted alkyl esters, are especially preferred photosensitisers for use in the invention. Examples of such compounds include those of general formula I:

$$R^2{}_2N-CH_2COCH_2-CH_2CO-OR^1 \quad (I)$$

(wherein
$R^1$ represents a substituted or unsubstituted, preferably substituted, straight-chained, branched or cyclic alkyl group (e.g. a substituted straight-chained alkyl group); and each $R^2$ independently represents a hydrogen atom or an optionally substituted alkyl group, e.g. a group $R^1$) and pharmaceutically acceptable salts thereof.

As used herein, the term "alkyl", unless stated otherwise, includes any long or short chain, cyclic, straight-chained or branched aliphatic saturated or unsaturated hydrocarbon group. The unsaturated alkyl groups may be mono- or polyunsaturated and include both alkenyl and alkynyl groups. Unless stated otherwise, such groups may contain up to 40 atoms. However, alkyl groups containing up to 30, preferably up to 10, particularly preferably up to 8, especially preferably up to 6, e.g. up to 4 carbon atoms are preferred.

The substituted alkyl $R^1$ and $R^2$ groups may be mono or poly-substituted. Suitable substituents may be selected from hydroxy, alkoxy, acyloxy, alkoxycarbonyloxy, amino, aryl, nitro, oxo, fluoro, $-SR_3$, $-NR^3{}_2$ and $-PR^3{}_2$ groups, and each alkyl group may be optionally interrupted by one or more $-O-$, $-NR_3-$, $-S-$ or $-PR_3-$ groups, in which $R^3$ is a hydrogen atom or a $C_{1-6}$ alkyl group).

Preferred substituted alkyl $R^1$ groups include those carrying one or more oxo groups, preferably straight-chained $C_{4-12}$ alkyl (e.g. $C_{8-10}$ alkyl) groups substituted by one, two or three (preferably two or three) oxo groups. Examples of such groups include 3,6-dioxa-1-octyl and 3,6,9-trioxa-1-decyl groups.

Particularly preferred for use in the invention are those compounds of formula I in which at least one $R^2$ represents a hydrogen atom. In especially preferred compounds each $R^2$ represents a hydrogen atom.

Compounds of formula I in which $R^1$ represents an unsubstituted alkyl group (preferably $C_{1-8}$ alkyl, e.g. $C_{1-6}$ alkyl) or more preferably an alkyl group (e.g. $C_{1-2}$ alkyl, especially $C_1$ alkyl) substituted by a substituent as hereinbefore defined (e.g. by an aryl group such as phenyl or by an alkoxy group such as methoxy) are also preferred.

Unsubstituted alkyl groups which may be used in the invention include both branched and straight-chained hydrocarbon groups. Compounds of formula I in which $R^1$ is a $C_{4-8}$, preferably a $C_{5-8}$, straight chain alkyl group which is branched by one or more $C_{1-6}$ (e.g. $C_{1-2}$ alkyl) groups are preferred. Representative examples of suitable unsubstituted branched alkyl groups include 2-methylpentyl, 4-methylpentyl, 1-ethylbutyl and 3,3-dimethyl-1-butyl. 4-methylpentyl is particularly preferred.

Compounds of formula I in which $R^1$ is a $C_{1-10}$ straight-chained alkyl group are also preferred. Representative examples of suitable unsubstituted alkyl groups include methyl, ethyl, propyl, butyl, pentyl, hexyl and octyl (e.g. n-propyl, n-butyl, n-pentyl, n-hexyl and n-octyl). Hexyl, especially n-hexyl, is a particularly preferred group. Methyl is also particularly preferred.

Particularly preferred for use in the invention are those compounds of formula I in which $R^1$ represents a $C_{1-2}$ alkyl group (preferably a $C_1$ alkyl group) optionally substituted by an aryl group.

Still further preferred for use in the invention are those compounds of formula I in which $R^1$ represents an alkyl group (e.g. $C_{1-2}$ alkyl, especially $C_1$ alkyl) substituted by an aryl group (e.g. phenyl). Preferred substituted alkyl $R^1$ groups which may be present in compounds of formula I include $C_{1-6}$ alkyl, preferably $C_{1-4}$ alkyl, particularly preferably $C_1$ or $C_2$ alkyl (e.g. $C_1$ alkyl) substituted (preferably terminally substituted) by an optionally substituted aryl group.

By an "aryl group" is meant a group which is aromatic. Preferred aryl groups comprise up to 20 carbon atoms, more preferably up to 12 carbon atoms, for example, 10 or 6 carbon atoms.

Aryl groups which may be present in the compounds of the invention may be heteroaromatic (e.g. 5-7 membered heteroaromatics) but are preferably non-heteroaromatic. By "non-heteroaromatic" is meant an aryl group having an aromatic system comprising electrons originating solely from carbon atoms. Preferred aryl groups include phenyl and napthyl, especially phenyl. In preferred compounds for use in the invention one or two aryl groups may be present, preferably one.

In a preferred aspect the invention provides the use of a photosensitiser which is a compound of formula I wherein $R^1$ represents an aryl substituted $C_{1-4}$ alkyl group (preferably $C_{1-2}$, e.g. $C_1$), preferably wherein said aryl group comprises up to 20 carbon atoms (e.g. up to 12 carbon atoms, especially 6 carbon atoms) and is itself optionally substituted, and each $R^2$ is as hereinbefore defined (e.g. each $R^2$ is hydrogen), or a pharmaceutically acceptable salt thereof in the manufacture of a medicament for use in the prevention or treatment of acne.

Aryl groups which may be present in the compounds of the invention may optionally be substituted by one or more (e.g. 1 to 5), more preferably one or two, groups (e.g. one group). Preferably the aryl group is substituted at the meta or para position, most preferably the para position. Suitable substituent groups may include haloalkyl (e.g. trifluoromethyl), alkoxy (i.e. —OR groups wherein R is preferably a $C_{1-6}$ alkyl group), halo (e.g. iodo, bromo, more especially chloro and fluoro), nitro and $C_{1-6}$ alkyl (preferably $C_{1-4}$ alkyl). Preferred $C_{1-6}$ alkyl groups include methyl, isopropyl and t-butyl, particularly methyl. Particularly preferred substituent groups include chloro and nitro. Still more preferably the aryl group is unsubstituted.

Preferred compounds for use in the invention include methyl ALA ester, ethyl ALA ester, propyl ALA ester, butyl ALA ester, pentyl ALA ester, hexyl ALA ester, octyl ALA ester, 2-methoxyethyl ALA ester, 2-methylpentyl ALA ester, 4-methylpentyl ALA ester, 1-ethylbutyl ALA ester, 3,3-dimethyl-1-butyl ALA ester, benzyl ALA ester, 4-isopropylbenzyl ALA ester, 4-methylbenzyl ALA ester, 2-methylbenzyl ALA ester, 3-methylbenzyl ALA ester, 4-[t-butyl]benzyl ALA ester, 4-[trifluoromethyl]benzyl ALA ester, 4-methoxybenzyl ALA ester, 3,4-[di-chloro]benzyl ALA ester, 4-chlorobenzyl ALA ester, 4-fluorobenzyl ALA ester, 2-fluorobenzyl ALA ester, 3-fluorobenzyl ALA ester, 2,3,4,5,6-pentafluorobenzyl ALA ester, 3-nitrobenzyl ALA ester, 4-nitrobenzyl ALA ester, 2-phenylethyl ALA ester, 4-phenylbutyl ALA ester, 3-pyridinyl-methyl ALA ester, 4-diphenyl-methyl ALA ester and benzyl-5-[(1-acetyloxyethoxy)-carbonyl]amino levulinate.

Still further preferred compounds for use in the invention include methyl ALA ester, ethyl ALA ester, 2-methoxyethyl ALA ester, benzyl ALA ester, 4-isopropylbenzyl ALA ester, 4-methylbenzyl ALA ester, 2-methylbenzyl ALA ester, 3-methylbenzyl ALA ester, 4[t-butyl]benzyl ALA ester, 4-[trifluoromethyl]benzyl ALA ester, 4-methoxybenzyl ALA ester, 3,4[di-chloro]benzyl ALA ester, 4-chlorobenzyl ALA ester, 4-fluorobenzyl ALA ester, 2-fluorobenzyl ALA ester, 3-fluorobenzyl ALA ester, 2,3,4,5,6-pentafluorobenzyl ALA ester, 3-nitrobenzyl ALA ester, 4-nitrobenzyl ALA ester, 2-phenylethyl ALA ester, 4-phenylbutyl ALA ester, 3-pyridinyl-methyl ALA ester, 4-diphenyl-methyl ALA ester and benzyl-5-[(1-acetyloxyethoxy)-carbonyl]amino levulinate.

Particularly preferred compounds for use in the invention include benzyl ALA ester, 4-isopropylbenzyl ALA ester, 4-methylbenzyl ALA ester, 2-methylbenzyl ALA ester, 3-methylbenzyl ALA ester, 4-[t-butyl]benzyl ALA ester, 4-[trifluoromethyl]benzyl ALA ester, 4-methoxybenzyl ALA ester, 3,4-[di-chloro]benzyl ALA ester, 4-chlorobenzyl ALA ester, 4-fluorobenzyl ALA ester, 2-fluorobenzyl ALA ester, 3-fluorobenzyl ALA ester, 2,3,4,5,6-pentafluorobenzyl ALA ester, 3-nitrobenzyl ALA ester, 4-nitrobenzyl ALA ester, 2-phenylethyl ALA ester, 4-phenylbutyl ALA ester, 3-pyridinyl-methyl ALA ester, 4-diphenyl-methyl ALA ester and benzyl-5-[(1-acetyloxyethoxy)-carbonyl]amino levulinate.

Especially preferred compounds for use in the methods herein described include benzyl ALA ester, 4-isopropylbenzyl ALA ester and 4-methylbenzyl ALA ester, especially benzyl ALA ester. 4-Nitrobenzyl ALA ester, 4-chlorobenzyl ALA ester and benzyl ALA ester are especially preferred.

The compounds for use in the invention may be prepared by any conventional procedure available in the art (e.g. as described in WO02/10120 to PhotoCure ASA). For example, esters of 5-ALA may be prepared by reaction of 5-ALA with the appropriate alcohol in the presence of base. Alternatively compounds for use in the invention may be available commercially (e.g. from PhotoCure ASA, Norway).

The compounds for use according to the method of the invention may be in the form of a free amine (e.g. —$NH_2$, —$NHR^2$ or —$NR^2R^2$) or preferably in the form of a physiologically acceptable salt. Such salts preferably are acid addition salts with physiologically acceptable organic or inorganic acids. Suitable acids include, for example, hydrochloric, nitric, hydrobromic, phosphoric, sulphuric, sulphonic and sulphonic acid derivatives. Particularly preferred salts are acid addition salts with sulphonic acid or sulphonic acid derivatives as described in WO2005/092838 to PhotoCure ASA, the entire contents of which are incorporated herein by reference. Procedures for salt formation are conventional in the art.

In the method of the invention a single photosensitiser (i.e. a derivative of 5-ALA) may be used alone in treating or preventing acne. Alternatively, a combination of two or more, preferably two, photosensitisers may be used wherein at least one of the photosensitisers is a derivative of 5-ALA or a pharmaceutically acceptable salt thereof.

Other photosensitisers which may be formulated with a derivative of 5-ALA (e.g. a 5-ALA ester) or co-administered in accordance with the invention include:

Hematoporphyrin derivative (HpD);

Hematoporphyrins such as Photofrin® (Quadra Logic Technologies Inc., Vancouver, Canada) and Hematoporphyrin IX (HpIX);

Photosan III (Seehof Laboratorium GmbH, Seehof, Wesselburenerkoog, Germany);

Chlorins such as tetra(m-hydroxyphenyl)chlorins (m-THPC) and their bacteriochlorins (Scotia Pharmaceuticals Ltd, Surrey, UK), mono-L-aspartyl chlorin e6 (NPe6) (Nippon Petrochemical Co., CA, USA), chlorin e6 (Porphyrin Products Inc.), benzoporphyrins (Quadra Logic Technologies Inc., Vancouver, Canada) (e.g. benzoporphyrin derivative monoacid ring A, BPD-MA) and purpurines (PDT Pharmaceuticals Inc., CA, USA) (e.g. tin-ethyl etiopurpurin, SnET2);

phthalocyanines (e.g. zinc-(Quadra Logic Technologies Inc., Vancouver, Canada), some aluminium- or silicon phthalocyanines, which may be sulfonated, in particular sulfonated phthalocyanines such as aluminium phthalocyanine di-sulfonate ($AlPcS_{2a}$) or aluminium phthalocyanine tetra-sulfonate ($AlPcS_4$));

porphycenes;

hypocrellins;

Protoporphyrin IX (PpIX);

Hematoporphyrin di-ethers;

Uroporphyrins;

Coproporphyrins;

Deuteroporphyrin;

Polyhematoporphyrin (PHP), and precursors and derivatives thereof; and antibiotics such as tetracycline (e.g. Topicycline®, Shire).

Preferably the second photosensitiser will be a Hematoporphyrin (e.g. Photofrin®), a chlorin (particularly m-THPC or chlorin e6) or a sulphonated phthalocyanine (particularly aluminium phthalocyanine di-sulfonate or aluminium phthalocyanine tetra-sulfonate).

In a further aspect the invention thus provides the use of a first photosensitiser which is a derivative of 5-ALA as hereinbefore defined, or a pharmaceutically acceptable salt thereof, together with a second photosensitiser in the manufacture of a medicament for use in the prevention or treatment of acne.

In a yet further aspect the invention provides the use of a first photosensitiser which is a derivative of 5-ALA as hereinbefore defined, or a pharmaceutically acceptable salt thereof, together with a second photosensitiser in the manufacture of medicaments for simultaneous, separate or sequential use in a method of treating or preventing acne.

In a still further aspect the invention provides a kit or pack containing a first photosensitiser which is a derivative of 5-ALA as hereinbefore defined, or a pharmaceutically acceptable salt thereof, and separately a second photosensitiser for simultaneous, separate or sequential use in a method of treating or preventing acne.

As used herein, "prevention" of acne means prophylactic treatment of acne. Thus the compounds described herein may be used according to the invention for treatment of areas of the skin which need not necessarily have developed acne at the time of treatment, but which are prone to acne. Preferably, the compounds for use in accordance with the invention are for treatment of acne once established, in particular treatment of inflammatory acne.

As used herein, the term "acne" includes both inflammatory and non-inflammatory diseases of the pilosebaceous unit. Primarily, however, the methods herein described will be used for treating the more inflammatory types of acne where bacterial invasion of the pilosebaceous unit or follicles has occurred. As previously noted, the precise cause of acne is unknown though it is commonly associated with increased production of sebum (lipids secreted by the androgen-sensitive sebaceous glands), proliferation of bacteria such as *Propionibacterium* (e.g. *P. acnes, P. granulosum* and *P. avidum*), increased turnover of epithelial cells and/or the development of inflammation (e.g. redness, swelling and/or pus). The compounds described herein are preferably used for the treatment or prevention (preferably for the treatment) of acne associated with *Propionibacterium acnes*.

Acne can manifest itself in a number of different ways (see attached FIG. 1). Common characteristics of acne include blackheads (comedones) and whiteheads. These are caused by pores becoming clogged (e.g. with sebum and/or dead cells). If the pore stays open, a blackhead results (FIG. 1(*i*)), whereas if the pore closes and bulges out a whitehead is produced (FIG. 1(*ii*)). Papules, pustules and cysts are believed to be produced if the pore wall becomes damaged and bacteria infect the pore. In a papule the pus lies fairly close to the surface of the skin (FIG. 1(*iii*)) whereas in a pustule the pus is present deeper inside the pore (FIG. 1(*iv*)). Cysts are generally larger and deeper than pustules and contain large amounts of pus. The compounds described herein may be used for the treatment or prevention of one or more of the following: blackheads, whiteheads, papules, pustules and cysts.

Acne is categorised into different forms depending, for example, on the nature, severity and/or location of the blackheads, whiteheads, papules, pustules and/or cysts. Representative types of acne which may be treated according to the invention include acne vulgaris, acne rosacea, acne conglobate, acne papulosa and premenstrual acne, preferably acne vulgaris which is a chronic inflammatory disease of the pilosebaceous apparatus. Acne may occur on the back, chest, upper arms and/or face; the compounds described herein may be used for treating any of these areas of the body, especially the face.

Certain milder forms of acne (e.g. blackheads and/or whiteheads) may not always be considered to be a "disease" and treatment thereof may be carried out purely for cosmetic reasons. This might be the case, for example, when acne is relatively infrequent and/or not widespread (i.e. few spots occur).

Thus, viewed from a further aspect the invention provides a method of cosmetic treatment of acne (e.g. on the face), said method comprising administering (e.g. topically applying) to an affected site a photosensitiser which is a derivative (e.g. an ester) of 5-aminolevulinic acid (5-ALA) as hereinbefore defined, or a pharmaceutically acceptable salt thereof, and photoactivating said photosensitiser at the affected site.

The compounds for use according to the invention may be formulated in any conventional manner with one or more physiologically acceptable carriers or excipients according to techniques well known in the art.

Compositions may be administered systemically (e.g. orally or parenterally) or more preferably locally (e.g. by injection or more preferably topically) at or near the affected site. The route of administration will depend on the severity and nature of the acne to be treated, the location of the acne and the photosensitiser (or combination of photosensitisers) used. Generally, however, local administration, still more preferably topical application, will be preferred.

Preferred formulations include gels, creams, ointments, sprays, lotions, salves, sticks, soaps, powders, aerosols, drops, solutions and any other conventional pharmaceutical forms in the art. Gels, creams and ointments are generally preferred.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

The compositions may additionally include lubricating agents, wetting agents, emulsifying agents, suspending agents, preserving agents, flavouring agents, odour enhancers and/or adsorption enhancers, e.g. surface penetrating agents as mentioned below, and the like. The compositions for use in the method of the invention may be formulated so as to provide quick, sustained or delayed release of the active ingredient after administration to the patient by employing procedures well known in the art. Solubilizing and/or stabilizing agents may also be used, e.g. cyclodextrins (CD) $\alpha$, $\beta$, $\gamma$ and HP-cyclodextrin. Compositions may be in any appropriate dosage form, for example as an emulsion or in liposomes, niosomes, microspheres, nanoparticles or the like. The compound for use in the invention may then be absorbed to, incorporated in or bound to these forms.

Typically, compositions for PDT treatment of acne will be in the form of a ready-to-use formulation such as a cream or as a kit consisting of a two component system (e.g. containing two photosensitizing agents).

The pH in the final formulation is preferably in the range 2.5 to 7.4. Slightly acidic pH, for example pH 5-7, is preferred if the formulation is a ready-to-use formulation.

The concentration of the 5-ALA compounds described herein in the final formulation for treatment of acne will vary depending on several factors including the chemical nature of the compound, the chemical composition, mode of administration and nature of the acne to be treated. Generally, however, concentration ranges between 0.01 to 30% (w/w) are suitable. The most preferred concentrations for acne treatment with local administration is in the range 0.02 to 25% (w/w), e.g. about 5% (w/w).

After administration of the pharmaceutical formulation containing the photosensitiser(s), the site to be treated is exposed to light to achieve the desired photosensitizing effect. The length of time following administration at which the light exposure takes place will depend on the nature of the composition, the condition to be treated and the form of administration. Generally, it is necessary that the photosensitiser should reach an effective tissue concentration at the site of the acne prior to photoactivation. This can generally take in the region of from 0.5 to 24 hours (e.g. 1 to 3 hours).

In a preferred treatment procedure, the photosensitiser(s) is/are applied to the affected site followed by irradiation (e.g. after a period of about 3 hours). If necessary, this procedure may be repeated, e.g. up to a further 3 times, at intervals of up to 14 days (e.g. 7-14 days). In those cases where this procedure does not lead to a satisfactory reduction in, or complete healing of, the acne, an additional treatment may be performed several months later.

Methods for irradiation of different areas of the body, eg. by lamps or lasers are well known in the art (see for example Van den Bergh, Chemistry in Britain, May 1986 p. 430-439). The irradiation will in general be applied at a dose level of 40 to 200 Joules/cm$^2$, for example at 100 Joules/cm$^2$.

The wavelength of light used for irradiation may be selected to achieve a more efficacious photosensitizing effect. The most effective light is light in the wavelength range 300-800 nm, typically 400-700 nm.

A further aspect of the invention thus provides a method of treating acne in a human, said method comprising administering to the affected site a photosensitiser which is a derivative of 5-ALA or a composition as hereinbefore defined, and exposing said surface to light, preferably to light in the wavelength region 300-800 nm, for example 400-700 nm.

As hereinbefore described, the compounds for use in the invention may be formulated and/or administered with other photosensitizing agents, for example 5-ALA or another 5-ALA derivative, or a porphyrin derivative such as Photofrin®. Alternatively, the compounds for use according to the invention may be formulated and/or administered with other active components which are able to increase the photosensitizing effect and thus enhance the treatment of acne. For example, chelating agents may beneficially be included and/or co-administered in order to enhance the accumulation of Pp; the chelation of iron by the chelating agent prevents its incorporation into Pp to form haem by the action of the enzyme ferrochelatase, thereby leading to a build-up of Pp. The photosensitizing effect is thus enhanced.

Suitable chelating agents include aminopolycarboxylic acids, including any of the chelants described in the literature for metal detoxification or for the chelation of paramagnetic metal ions in magnetic resonance imaging contrast agents. Particular mention may be made of EDTA, CDTA (cyclohexane diamine tetraacetic acid), DTPA and DOTA and well known derivatives/analogues thereof. EDTA and DTPA are particularly preferred. To achieve the iron-chelating effect, desferrioxamine and other siderophores may also be used, e.g. in conjunction with aminopolycarboxylic acid chelating agents such as EDTA.

Where present, the chelating agent may conveniently be used at a concentration of 0.05 to 20%, e.g. 0.1 to 10% (w/w).

Penetration enhancers may also have a beneficial effect in enhancing the photosensitizing effect of the compounds for use in the invention. Surface-penetration assisting agents, especially dialkylsuphoxides such as dimethylsulphoxide (DMSO), may therefore also be included in the compositions for use in the invention and/or co-administered. The surface-penetration assisting agent may be any of the skin-penetration assisting agents described in the pharmaceutical literature e.g. chelators (e.g. EDTA), surfactants (e.g. sodium dodecyl sulphate), non-surfactants, bile salts (e.g. sodium deoxycholate) and fatty acids (e.g. oleic acid). Examples of appropriate surface penetrating assisting agents include isopropanol, HPE-101 (available from Hisamitsu), DMSO and other dialkylsulphoxides, in particular n-decylmethyl-sulphoxide (NDMS), dimethylsulphacetamide, dimethylformamide (DMFA), dimethylacetamide, glycols, various pyrrolidone derivatives (Woodford et al., *J. Toxicol. Cut. & Ocular Toxicology*, 1986, 5: 167-177), and Azone® (Stoughton et al., *Drug Dpv. Ind. Pharm.* 1983, 9: 725-744), or mixtures thereof.

The surface penetration agent may conveniently be provided in a concentration range of 0.2 to 50% (w/w), e.g. about 10% (w/w).

Viewed from a further aspect, the invention thus provides the use of a photosensitiser which is a derivative of 5-ALA (e.g. a 5-ALA ester), or a pharmaceutically acceptable salt thereof, together with at least one surface-penetration assisting agent, and optionally one or more chelating agents, in the manufacture of a medicament or medicaments for use in the treatment or prevention of acne.

The compounds for use in the invention may additionally be used in combination with other non-photosensitizing agents that improve treatment or prevention of acne. Such agents include one or more conventional acne treatment agents. Representative examples of such agents include:

Retinoids such as acitretin, isotretinion (e.g. Isotrex®, Steifel and Roaccutane®, Roche), tretinion (e.g. Retin-A®, Janssen-Cilag) and tazarotene;

Peroxides such as benzoyl peroxide (e.g. PanOxyl®, Stiefel);

Antibiotics such as tetracycline (e.g. Topicycline®, Shire), clindamycin (e.g. Dalacin T®, Pharmacia), erythromycin (e.g. Stiemycin®, Stiefel), doxycycline, oxytetracycline, minocycline, trimethoprim and metronidazole;

Hormones such as co-cyprindiol (cyproterone acetate with ethinyllestradiol), e.g. Dianette®, Schering Health;

Azelaic acid (e.g. Skinoren®, Schering Health) and derivatives thereof such as described in WO03/045893 to Photo-Cure ASA;

Adapalene (e.g. Differin®, Galderma);

Nicotinamide (e.g. Nican®, Dermal); and

Salicyclic acid (e.g. Acnisal®, DermaPharm).

Although these acne treatment agents may be present as part of the formulation, typically these will be used as a separate treatment to be administered simultaneously, separately or sequentially. Administration of any supplementary agent should be performed in terms of route, concentration and formulation, according to known methods for using these agents. These additional agents may be administered before, during or after PDT, depending on their function.

Viewed from a further aspect the invention thus provides a product or kit for use in a method of treating or preventing acne comprising:

(a) a first container containing a photosensitiser which is a derivative (e.g. an ester) of 5-ALA, or a pharmaceutically acceptable salt thereof; and (b) a second container containing a non-photosensitising acne treatment agent.

Additional components of the kit may also be provided such as a second photosensitizing agent, a surface-penetrating agent or a chelating agent as herein described.

In a further aspect the invention thus provides the use of a photosensitiser which is a derivative of 5-ALA (e.g. a 5-ALA ester), or a pharmaceutically acceptable salt thereof, together with a non-photosensitising acne treatment agent in the manufacture of a medicament or medicaments for use in the prevention or treatment of acne.

In a yet further aspect the invention provides the use of a photosensitiser which is a derivative of 5-ALA (e.g. a 5-ALA ester), or a pharmaceutically acceptable salt thereof, together with a non-photosensitising acne treatment agent in the manufacture of medicaments for simultaneous, separate or sequential use in a method of treating or preventing acne.

Depending on the nature of the acne to be treated, and the nature of any additional active agent or agents to be used in the method of the invention, this may be co-administered with the 5-ALA derivative, for example in a single composition, or this may be administered sequentially or separately. Typically, in those cases where a surface-penetration assisting agent is used, this will be administered in a separate step prior to administration of the compounds for use in the invention. When a surface-penetration assisting agent is used in pre-treatment this may be used at high concentrations, e.g. up to 100% (w/w). If such a pre-treatment step is employed, the photosensitizing agent may subsequently be administered up to several hours following pre-treatment, e.g. at an interval of 5-60 minutes following pre-treatment.

The invention will now be described in more detail by way of the following non-limiting Examples and with reference to the accompanying figures, in which.

GENERAL METHODS

Figure 1:
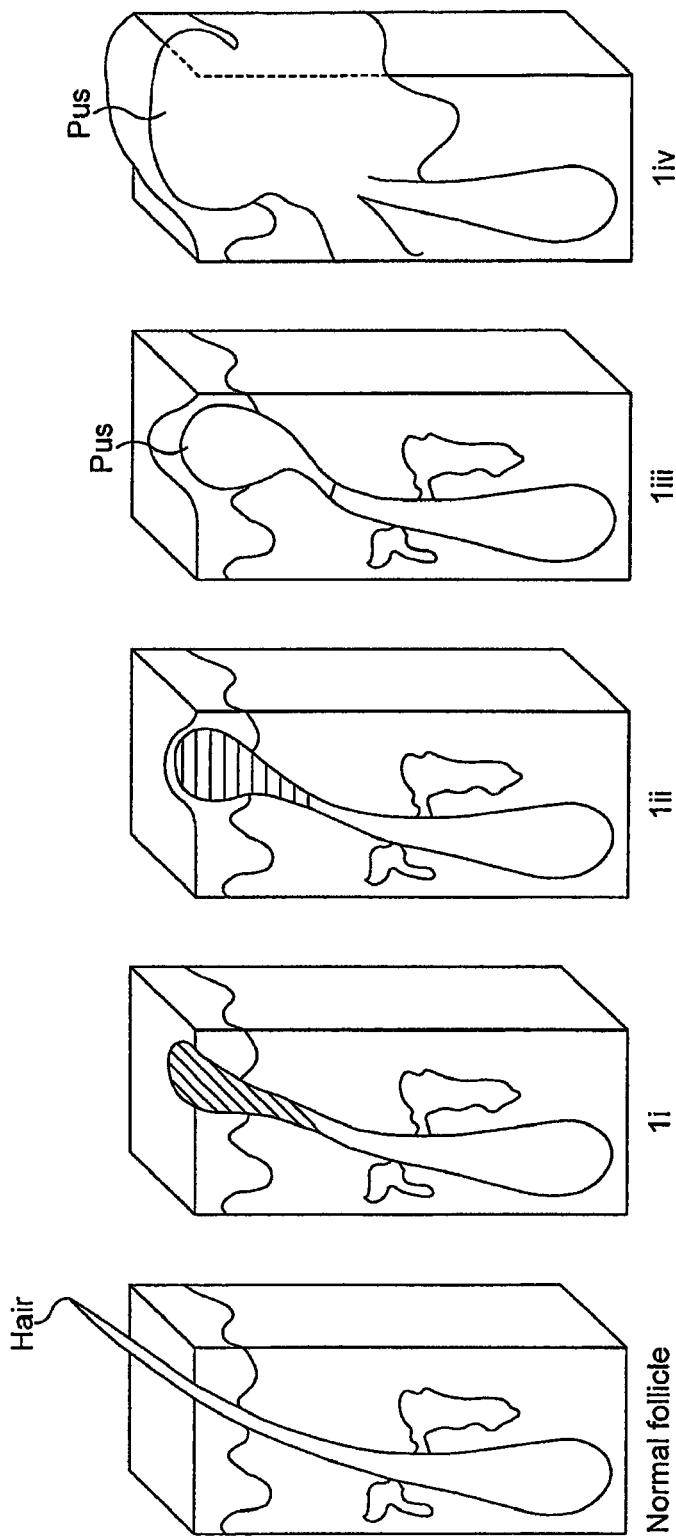
FIG. 1 shows different stages of acne.

Bacteria Cultures:

*Propionibacterium acnes* (*P. acnes*) was obtained from American Type Culture Collection (ATCC No. 6919), and bacteria were grown anaerobically in the dark on blood-agar plates at 37° C.

References: Skerman V B et al., *Int. J. Syst. Bacteriol.* 30: 225-420, 1980; Goodsell M E et al., *Curr. Microbiol.* 22: 225-230, 1991; Zierdt C H et al., *Int. J. Syst. Bacteriol.* 18: 33-47, 1968; Douglas H D and Gunter S E, *J. Bacteriol.* 52: 15-23, 1946; Johnson J L and Cummins C S, *J. Bacteriol.* 109: 1047-1066, 1972; Wang R F et al., *Appl. Environ. Microbiol.* 62: 1242-1247, 1996.

*Propionibacterium granulosum* (*P. granulosum*) was obtained from American Type Culture Collection (ATCC No. 25564).

References: Johnson I L, et al., *J. Bacteriol.* 109(3): 1047-1066, 1972; Skerman V B, et al., *Int. J. Syst. Bacteriol.* 30: 225-420, 1980.

*Propionibacterium avidum* (*P. avidum*) was obtained from ATCC (ATCC No. 25577).

References: Goodsell M E, et al., *Curr. Microbiol.* 22(4): 225-230, 1991; Skerman V B, et al., *Int. J. Syst. Bacteriol.* 30: 225-420, 1980.

Incubation with ALA Esters

PIPES buffer (ca. 1 ml) was added to each blood-agar petri-plate and with the help of a sterile glass-rod and a Pasteur pipette, the bacteria solution was transferred to a 20 ml test-tube. The suspension was then diluted with PIPES buffer until the optical density (OD) was 1.00±0.01 at 550 nm as measured by a spectrophotometer. At this OD the bacteria density is approximately $5 \times 10^8$ cells per ml.

A bacteria sample (100 µl of the suspension containing approx. $5 \times 10^8$ bacteria per ml) was collected and used as a t=0 control. Aliquots of the bacteria suspension were mixed with suitable volumes of the stock solutions of 5-ALA esters (containing 100 mM ALA ester) to obtain the appropriate concentrations and incubated for 4 hours at 37° C. in the dark. If illumination was not performed, survival was then assessed as described below.

Illumination

In some cases, illumination was performed on the bacteria-suspensions treated with ALA esters. The exact conditions are described in the Examples below. After illumination, survival was assayed as described below.

Survival Assay

After treatment with ALA esters (with or without illumination), the treated bacteria samples (as well as untreated controls) were collected and further diluted with PIPES buffer to $1 \times 10^4$ bacteria per ml. Aliquots of 20 ml of this suspension were then transferred to Bactoagar Petri-dishes (Futsaether et al., *Can. J. Microbiol.*, 39(2): 180-186 1993), and incubated for 3-5 days at 37° C. in the dark. The colonies formed on the Bactoagar Petri-plates were counted using a colony counter. Cell survival after incubation with different concentrations of 5-ALA esters is given relative to the control samples (i.e. samples collected at t=0 hrs and the sample collected after 4 hrs incubation without 5-ALA ester) and given as percent survival:

$$\text{Survival} = [C_{treated}/C_{control}] \times 100\%$$

where C=number of colonies.

Example 1

Dark Toxicity

In order to find suitable conditions for studying the photodynamic effect in *P. acnes* after incubation with ALA esters, a study was performed to assay the toxicity of the esters. This was done in the dark to avoid any PDT effect caused by stray light. Incubations and survival was assayed as described in the general section above, and the results are given in attached FIG. 2.

Figure 2:
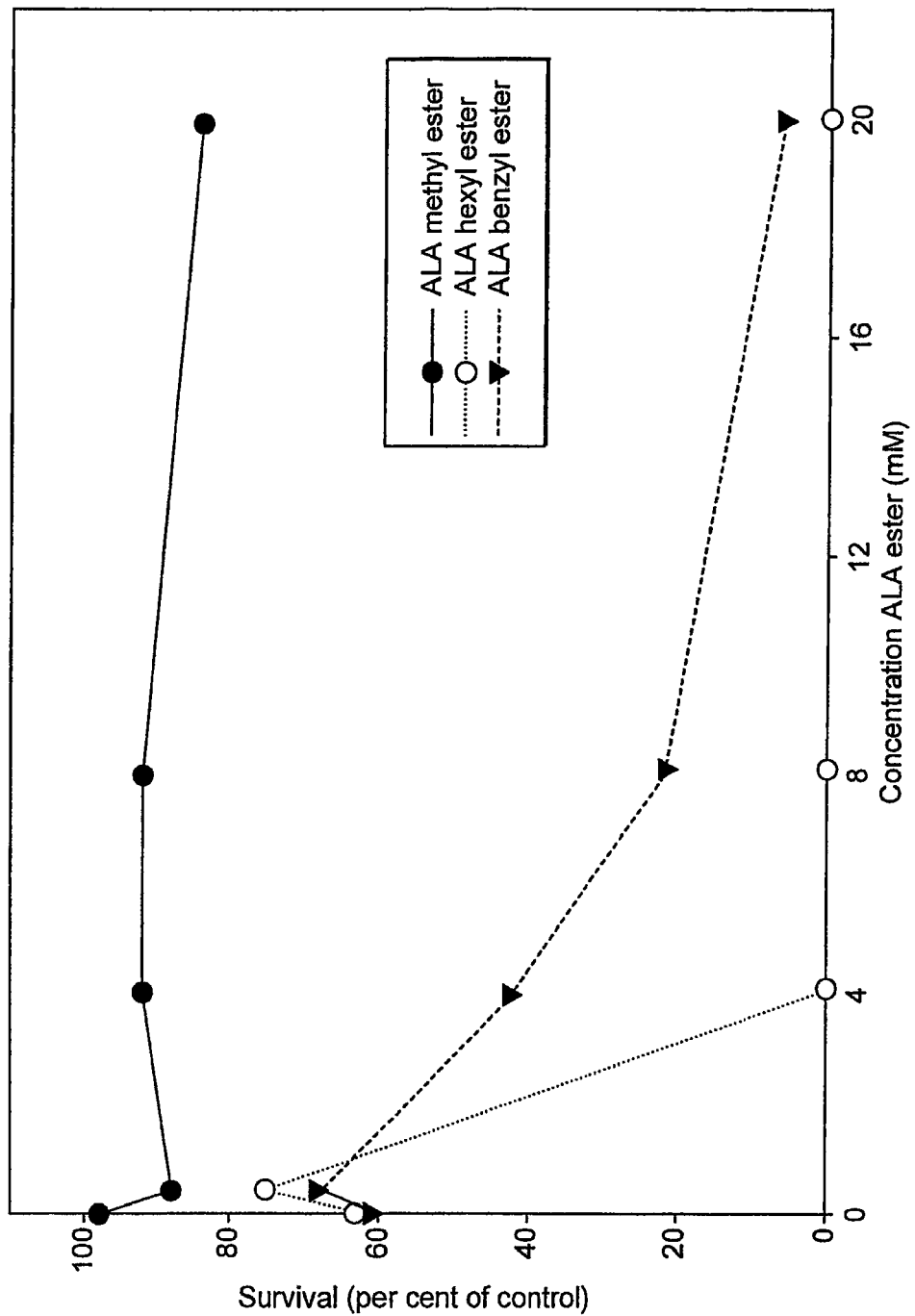
FIG. 2 shows dark toxicity results for ALA methyl-, ALA hexyl- and ALA benzyl esters.

It can be seen from FIG. 2 that the methyl ester was essentially non-toxic for concentrations up to 20 mM, whereas the ALA hexyl ester was very toxic. The ALA benzyl ester displayed intermediate toxicity.

Example 2

PDT with Curelight Broadband Lamp

Bacteria suspensions (*P. acnes*) were treated with 4 mM ALA methyl ester, 4 mM benzyl ester and 1 mM hexyl ester (due to high dark toxicity results for this ester) as described in the general section above, diluted and illuminated using a CureLight BroadBand lamp (available from PhotoCure ASA, Norway, red light of 580-740 nm and a fluence rate of ≤840 W/m$^2$) under temperature controlled conditions (e.g. at ambient temperature). During illumination, 2×20 μl aliquots were collected every second minute for at total of 10 minutes and assayed for survival as described in the general section above. Relative survival after illumination was calculated relative to the control sample without red light exposure. The results are shown in FIG. 3.

Figure 3:
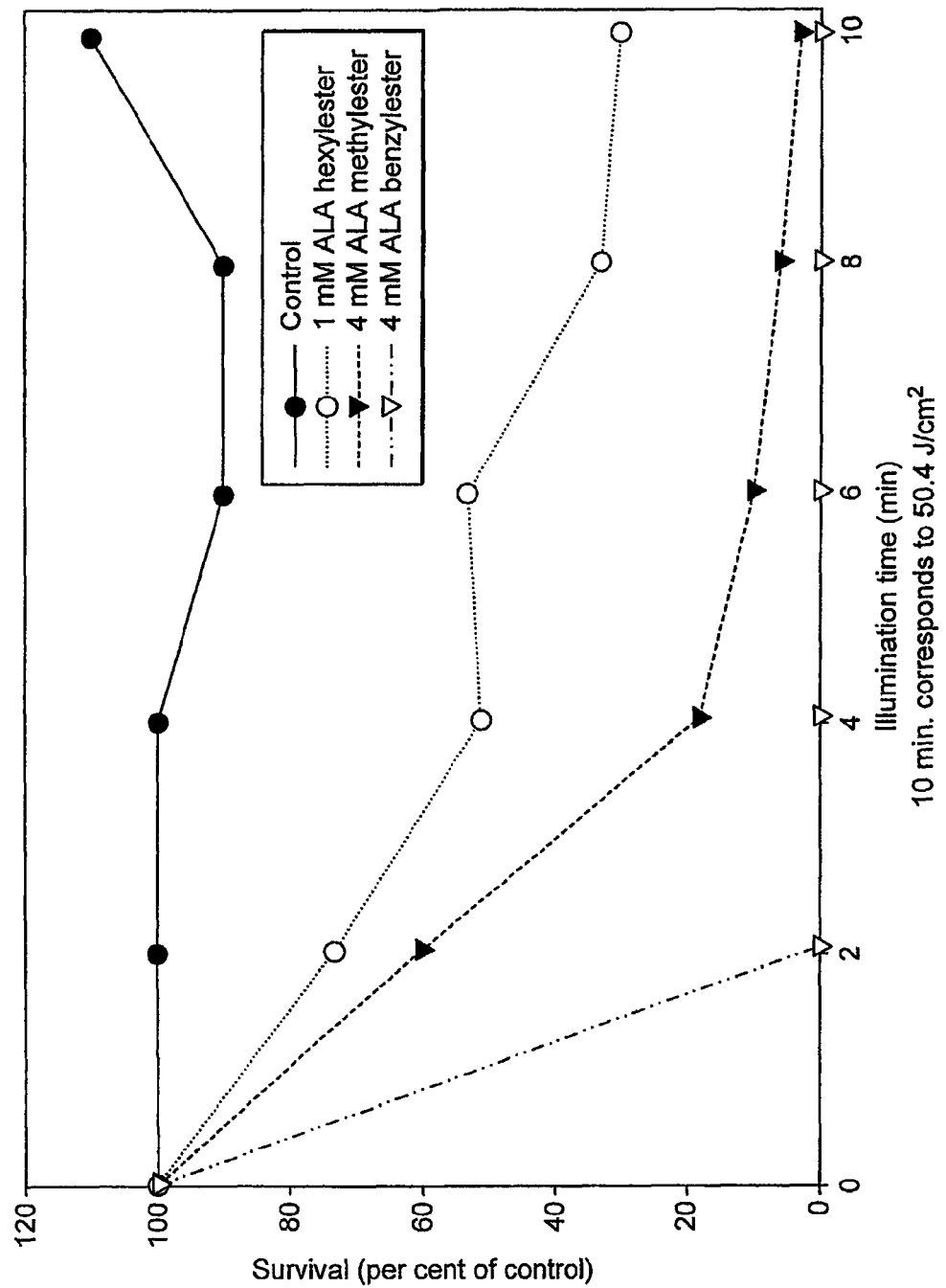
FIG. 3 shows photodynamic effects in *P. acnes* bacteria incubated with ALA methyl-, ALA hexyl- and ALA benzyl esters.

It can be seen in FIG. 3 that ALA benzyl ester was the most effective to kill the bacteria, whereas ALA methyl ester was the least effective. With 4 mM ALA benzyl ester, a light dose of approx. 10 J/cm$^2$ was sufficient to obtain 100% kill. ALA hexyl ester was also quite effective, but this ester was used in a lower concentration (1 mM) due to its high dark toxicity.

Example 3

PDT with Curelight LED Lamp (Sold Under the Tradename Aktilite by PhotoCure ASA)

In order to compare the ALA hexyl ester and the ALA benzyl ester at the same concentration (1 mM), and also to test another light source, another experiment involving the use of a narrow-band red light (CureLight LED 128 lamp sold under the tradename Aktilite by Photocure ASA, Norway) was conducted. This lamp consists of 128 light emitting diodes (LED) and has a peak wavelength of 634±3 nm. The emission spectrum of the lamp has a full width at half maximum (FWHM) of 18 nm. The fluence rate at 50 mm distance is approx. 50 mW/cm$^2$ (max. fluence rate variation of the target area is ±10%).

After incubation with the ALA esters, 10 ml bacterial suspensions were irradiated in a 5.5 cm plastic petri-dish (see general section above). The petri-dishes were placed on a support lying in a large water-reservoir at ambient temperature in order to avoid temperature effects. During illumination, 2×20 μl aliquots were collected every second minute for at total of 10 minutes and transferred to Bactoagar Petri-dishes. After 3-5 days of incubation (at 37° C. in the dark) the survival was determined as described in the general section and given relative to the non-illuminated control sample. The results are shown in FIG. 4.

Figure 4:
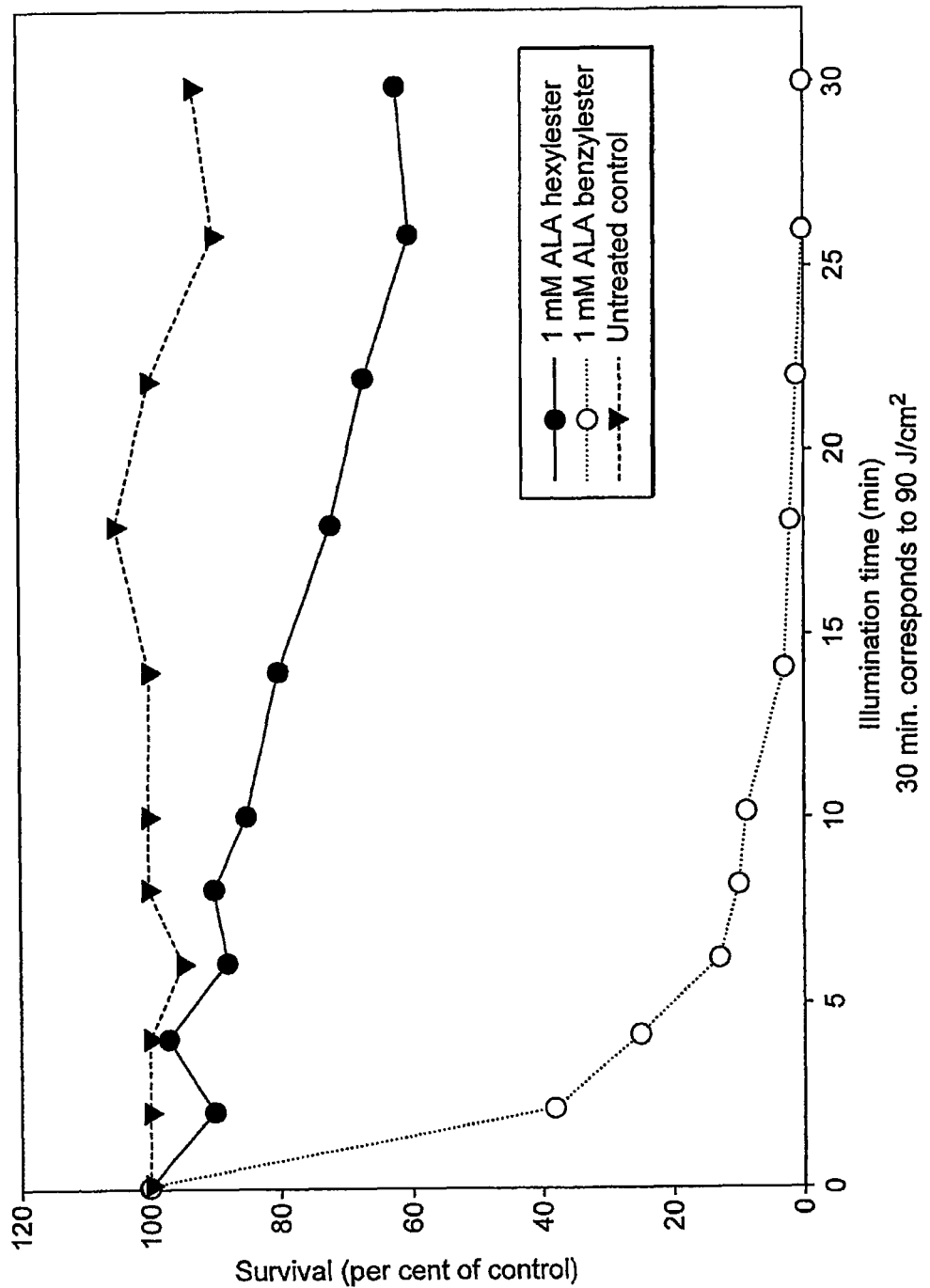
FIG. 4 shows photodynamic effects in bacteria incubated with ALA hexyl- and ALA benzyl esters.

It can be seen from FIG. 4 that 1 mM ALA benzyl ester gave a much better photodynamic effect than 1 mM ALA hexyl ester. In fact, 26 minutes of illumination (corresponding to a light fluence of 78 J/cm$^2$) killed all bacteria incubated with 1 mM ALA benzyl ester, but only 40% of the bacteria incubated with 1 mM ALA hexyl ester.

Example 4

Intracellular Porphyrin Formation

To study the intracellular porphyrin formation after incubation with the ALA esters, bacteria (5×10$^8$ cells per ml, 10 ml) were incubated with ALA esters at 37° C. in the dark for four hours. The formation of porphyrins was followed by studying the fluorescence emission spectra (the porphyrins display characteristic peaks). The procedure was as follows:

To assess the amount of endogenously retained porhyrins, 8 ml of the 5-ALA ester incubated bacteria were added to plastic test-tubes and incubated at 2-3° C. in the refrigerator to halt further 5-ALA ester uptake and/or porhyrin formation. Then the cells from were pelleted by centrifugation (5000 g, 5 rain, 2-3° C.), the supernatant discarded and the cells resuspended in fresh buffer (8 ml) and mixed well. Aliquots of 2 ml bacterial suspension were transferred to standard disposable plastic cuvettes, and fluorescence emission spectra of the cell suspensions were determined in a Perkin Elmer LS 50B fluorescence spectrometer using the following settings:

Excitation wavelength, $\lambda_x$: 405 nm
Emission wavelength, $\lambda_e$: 550-700 nm
Excitation and emission slits: 5 nm
Emission monochromator speed: 300 nm/min The fairly broad range of wavelengths measured was motivated by the need to have a control of the autofluorescence from the bacteria, which is most easily discernable at the lower or higher wavelengths.

Figure 5:
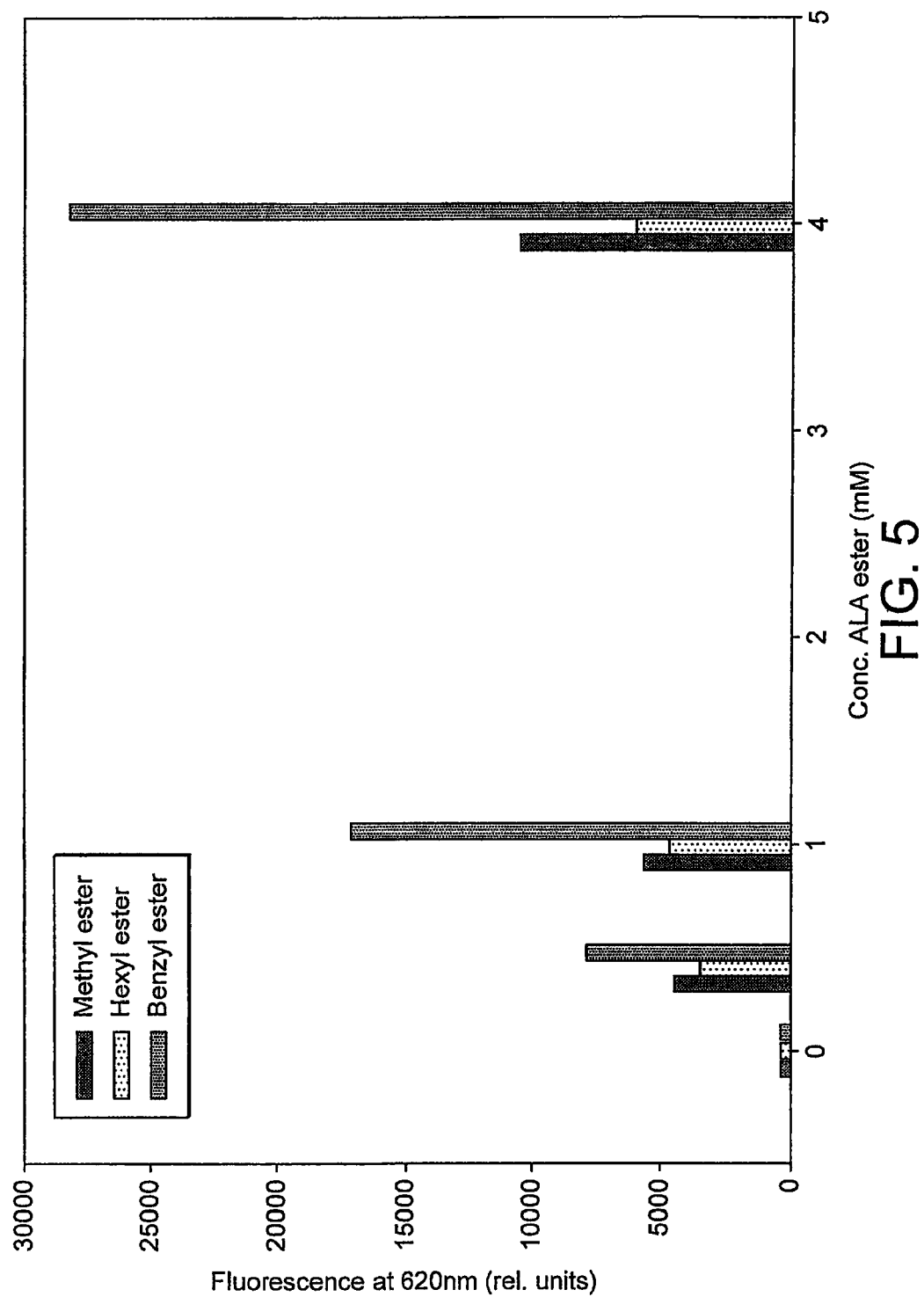
FIG. 5 shows porphyrin formation in *P. acnes* after incubation with various concentrations of ALA esters.

The results are shown in FIG. 5, from which it is evident that the ALA hexyl ester was the least effective in inducing porphyrin formation in *P. acnes*, probably due to high dark toxicity. The ALA methyl ester gave slightly higher porphyrin levels, but the ALA benzyl ester was by far the most effective inducer of bacterial porphyrin biosynthesis.

Example 5

Dark Toxicity

In order to find suitable conditions for studying the photodynamic effect in two other strains of "acne-associated bacteria", a study was performed to assay the toxicity of ALA hexylester and ALA benzyl ester in *P. granulosum* and *P. avidum*. This was done as described in Example 1, and the results are given in FIG. 6.

Figure 6:
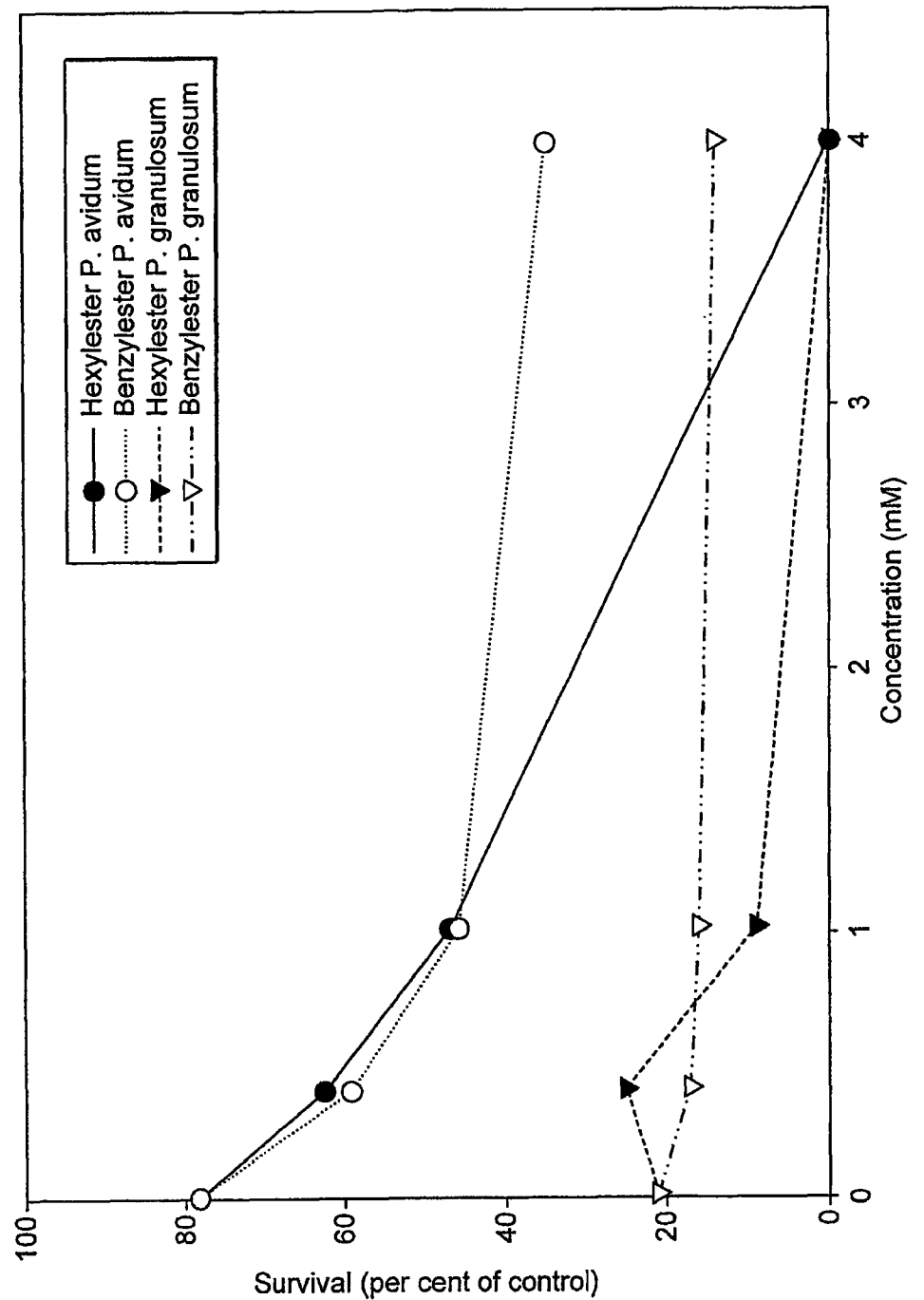
FIG. 6 shows dark toxicity of ALA hexyl- and ALA benzyl ester (survival is given relative to an untreated control, i.e. one which was not incubated for 4 hours in incubation buffer)

It is evident from FIG. 6 that ALA hexylester was considerably more toxic than ALA benzylester and that the hexylester at 4 mM killed 100% of both strains. It can also be seen that the strain *P. granulosum* did not tolerate the incubation conditions particularly well.

Example 6

PDT with Curelight Broadband Lamp

Bacteria suspensions (*P. granulosum* and *P. avidum*) were treated with 4 mM ALA methyl ester, 4 mM benzyl ester and 1 mM hexyl ester (due to high dark toxicity for this ester) as described in the general section above, diluted and illuminated using a CureLight BroadBand lamp (available from PhotoCure ASA, Norway—red light of 580-740 nm and a fluence rate of ≤840 W/m$^2$) under temperature controlled conditions (e.g. at ambient temperature).

Figure 7:
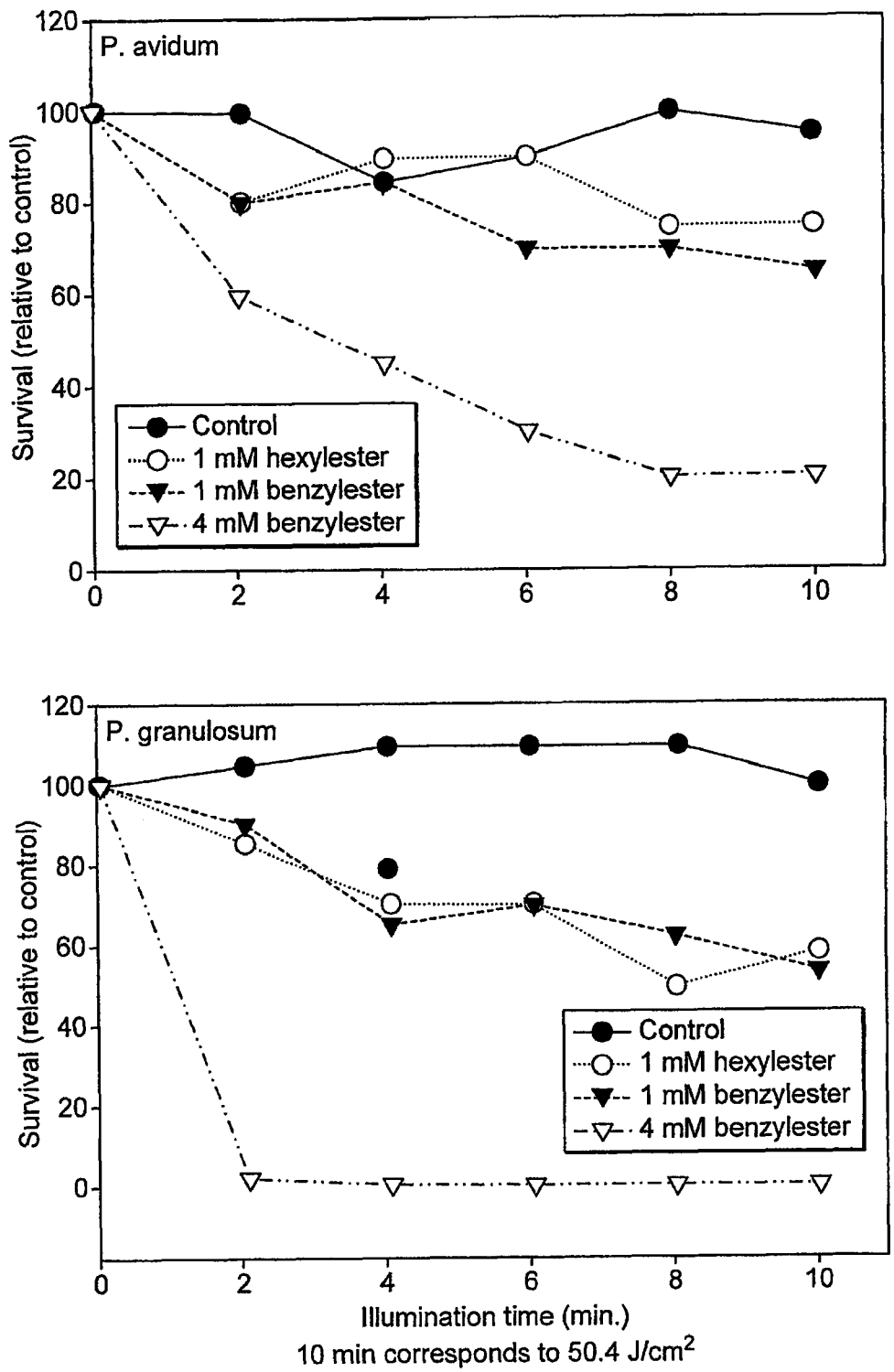
FIG. 7 shows photodynamic effects in *P. granulosum* and *P. avidum* bacteria incubated with ALA hexyl- and ALA benzyl esters.

Using the method described in Example 2, PDT effects in *P. granulosum* and *P. avidum* after incubation with ALA hexyl ester and ALA benzyl ester using the CureLight BroadBand lamp (PhotoCure ASA, Norway—red light of 580-740 nm and a fluence rate of ≤840 W/m$^2$) under temperature controlled conditions (e.g. at ambient temperature) were observed. The results appear in FIG. 7.

Example 7

PDT Effects with LED Lamp

Figure 8:
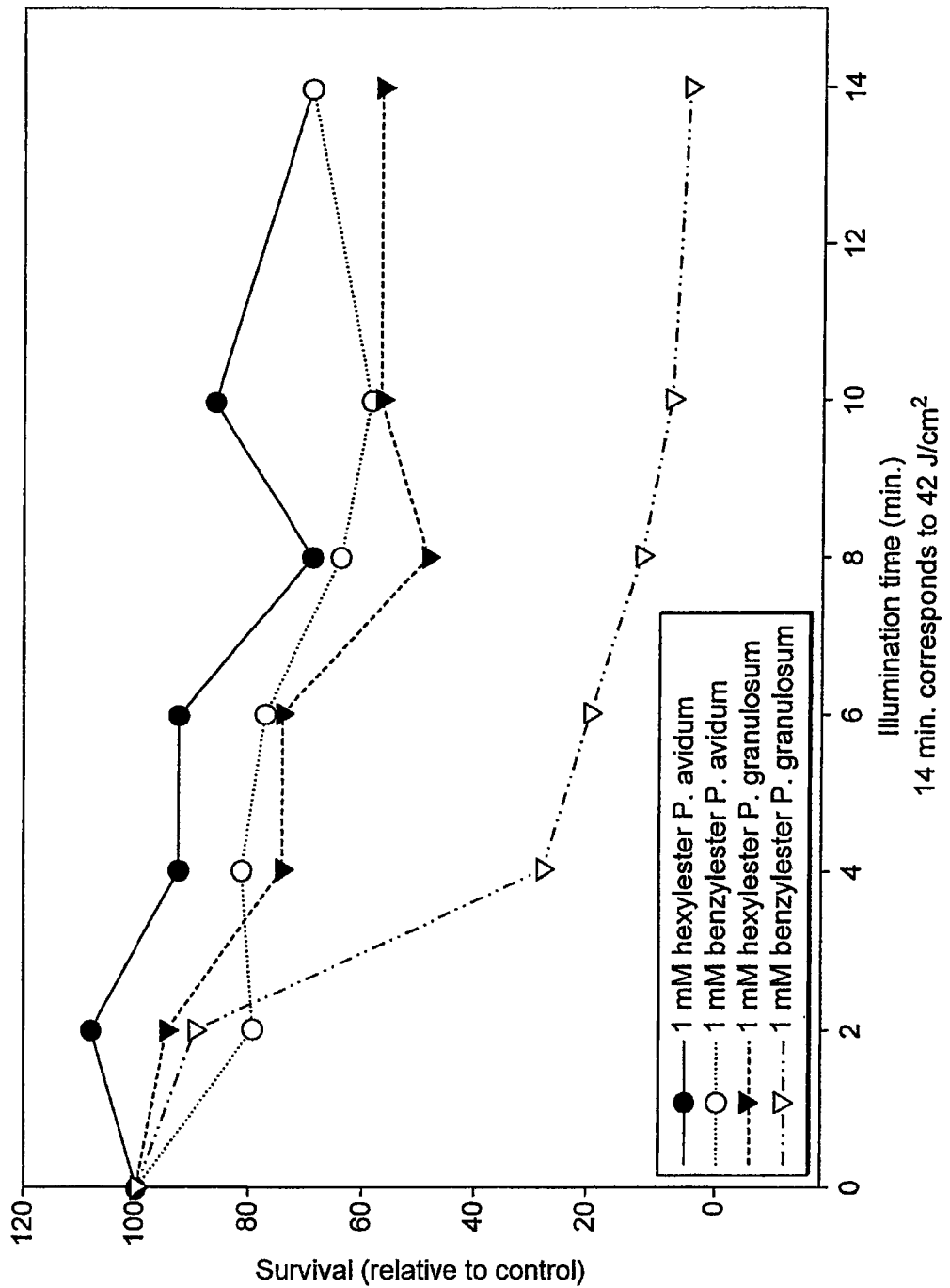
FIG. 8 shows photodynamic effects in *P. granulosum* and *P. avidum* with CureLight LED lamp (sold under the tradename Aktilite 128 by PhotoCure ASA) after incubation with ALA hexyl- and ALA benzyl esters.

PDT effects in *P. granulosum* and *P. avidum* after incubation with ALA hexyl ester and ALA benzyl ester (1 mM) were observed using the CureLight LED 128 lamp (sold under the tradename Aktilite by Photocure ASA, Norway) as described in Example 3. The experiment was performed as described in Example 3, and the results are shown in FIG. 8.

Example 8

Porphyrin Formation

This experiment was performed in *P. granulosum* and *P. avidum* and involved the following esters of ALA: Hexyl 5-aminolevulinate, benzyl 5-aminolevulinate, 3,6-dioxa-1-octyl 5-aminolevulinate, 4-isopropylbenzyl 5-aminolevulinate and 4-methylbenzyl 5-aminolevulinate.

The concentration of 1 mM for this experiment was chosen since the hexylester showed high dark toxicity at 4 mM (see Example 5). The experiment was performed as described in Example 4, and both the amount of endogenously retained porhyrins as well as the amount of exogenous porphyrins were determined by fluorescence spectroscopy.

Figure 9:
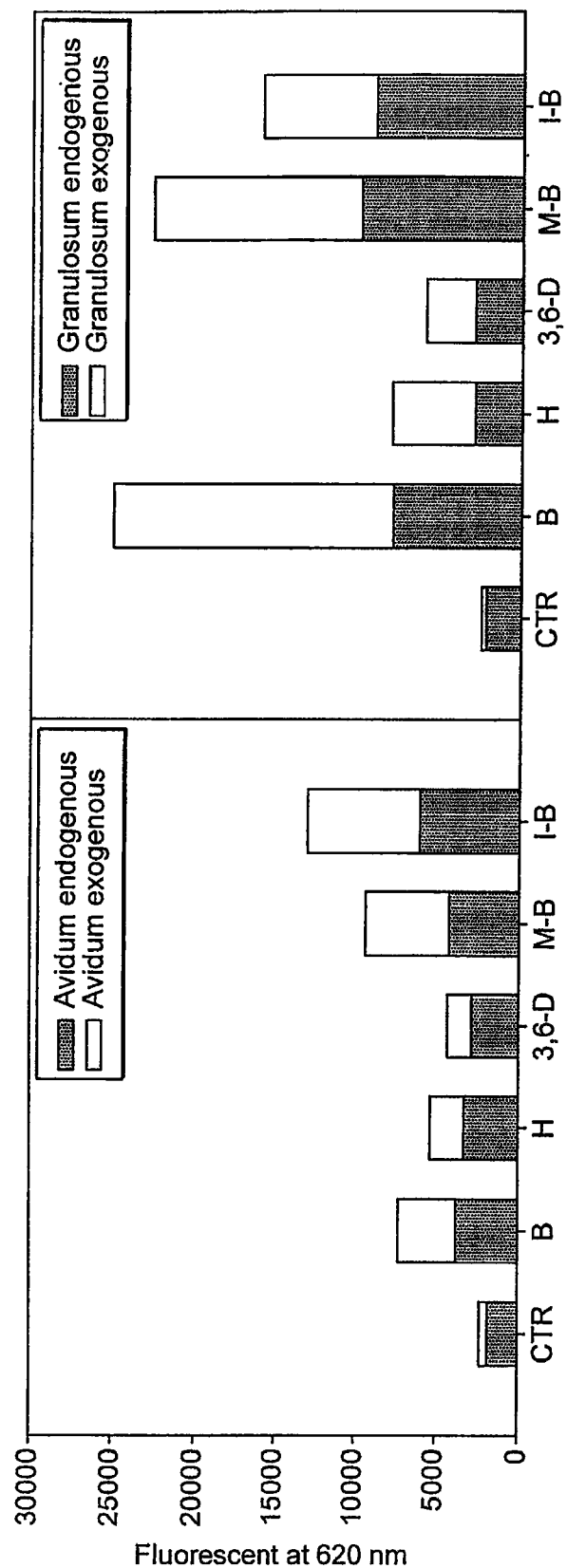
FIG. 9 shows porphyrin formation in *P. avidum* and *P. granulosum* after incubation with 1 mM benzyl—(B), hexyl—(H), 3,6-dioxa-1-octyl—(3,6-D), 4-methylbenzyl—(M-B) and 4-isopropylbenzyl—(I-B) esters of ALA.

The results are shown in FIG. 9 where the fluorescence at 620 nm has been used for quantification. Although there was a considerable difference between the two strains of bacteria with respect to porphyrin formation, it is evident from the Figure that the benzylesters had the greatest ability to induce porphyrin formation followed by the hexyl- and the 3,6-dioxa-1-octyl ester.

Example 9

Dark Toxicity

In order to find suitable conditions for studying the photodynamic effect in *P. acnes* after incubation with benzyl-, 4-chlorobenzyl-, 4-nitrobenzyl-, 2-methylbenzyl-, 4-methylpentyl- and 2-methoxyethyl 5-aminolevulinate, a study was performed to assay the toxicity of these compounds. This was done in the dark, as in Example 1, to avoid any PDT effect caused by stray light. Incubations and survival was assayed as described in the general section above, and the results are presented in Table 1 below.

TABLE 1

Summary of results for the dark toxicity experiments. Incubation with the ALA esters listed below occurred for 4 hours in the dark at 37° C. Cell survival was determined based on colony forming ability on agar plates. Mean normalised colony-forming units (CFU) based on 5-8 independent experiments with standard error of the means (SE) are presented.

| 5-ALA ester (side-chain) | Number of experiments | Concentration (mM) | % CFU | SE |
|---|---|---|---|---|
| Blank at t = 0 hr. | n = 4 | 0 | 100.0 | — |
| Blank at t = 4 hrs. | n = 4 | 0 | 82.9 | 6.6 |
| Benzyl | n = 5 | 0.4 | 78.3 | 8.4 |
|  | n = 5 | 4 | 62.9 | 16.8 |
|  | n = 5 | 20 | 15.0 | 6.9 |
| 4-chlorobenzyl | n = 5 | 0.4 | 81.6 | 10.4 |
|  | n = 5 | 4 | 3.7 | 1.7 |
|  | n = 5 | 20 | 0.0 | — |
| 4-nitrobenzyl | n = 8 | 0.4 | 63.5 | 11.9 |
|  | n = 8 | 4 | 61.8 | 12.1 |
|  | n = 8 | 20 | 53.2 | 13.4 |
| 2-methylbenzyl | n = 5 | 0.4 | 66.0 | 17.6 |
|  | n = 5 | 4 | 1.2 | 0.8 |
|  | n = 5 | 20 | 0.0 | — |
| 4-methylpentyl | n = 5 | 0.4 | 86.5 | 20.3 |
|  | n = 5 | 4 | 37.3 | 10.9 |
|  | n = 5 | 20 | 0.5 | 0.4 |
| 2-methoxyethyl | n = 8 | 0.4 | 75.5 | 13.9 |
|  | n = 8 | 4 | 60.8 | 18.4 |
|  | n = 8 | 20 | 54.0 | 11.4 |

The substances displayed quite different toxicities. The 4-nitrobenzyl and 2-methoxyethyl ALA esters showed almost no toxicity at concentrations up to 20 mM, whereas the 4-chlorobenzyl and the 2-methylbenzyl ALA esters showed considerable toxicity at 4 mM. Low toxicity was seen for all substances when tested at 0.4 mM, hence this concentration was chosen for the subsequent PDT experiments.

Example 10

PDT Effects with LED Lamp

Photodynamic inactivation of *P. acnes* after incubation with the 5-ALA esters listed in Example 9 (at 0.4 mM concentration) was studied following illumination with an Aktilite® 128 lamp. The lamp and the experimental details are described in Example 3, and the results are shown in FIG. 10.

Figure 10:
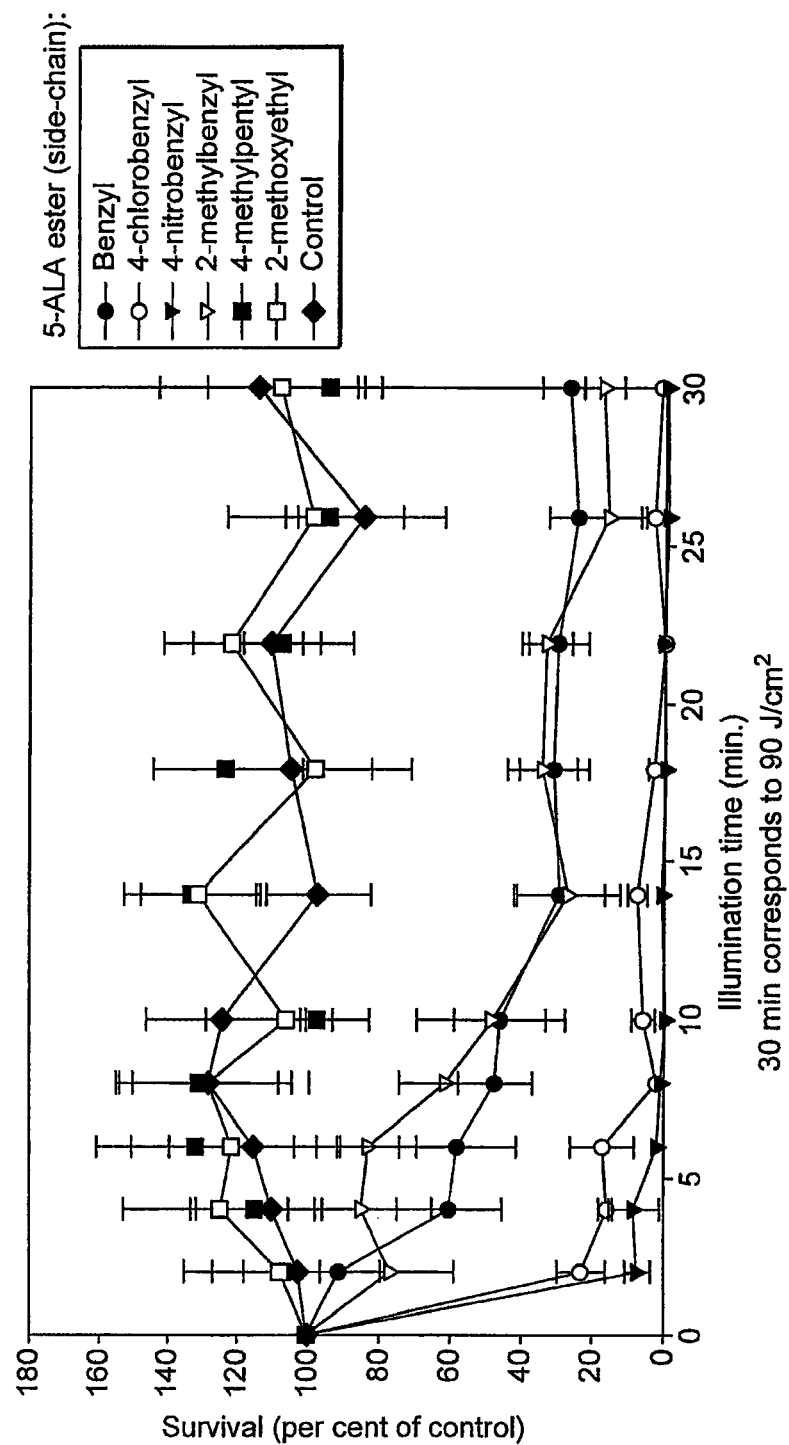
FIG. 10 shows photodynamic effects in *P. acnes* bacteria incubated with benzyl ALA ester, 4-chlorobenzyl ALA ester, 4-nitrobenzyl ALA ester, 2-methylbenzyl ALA ester, 4-methylpentyl ALA ester and 2-methoxyethyl ALA ester.

It can be seen from FIG. 10 that the 4-chlorobenzyl and the 4-nitrobenzyl ALA esters were the most efficient. In fact, only 10 minutes illumination was required to obtain practically 100% kill after incubation with 0.4 mM of these esters. At this concentration, the benzyl and the 2-methylbenzyl ALA esters showed good abilities to kill the bacteria (10 minutes illumination gave approx. 50 percent kill). A weaker PDT effect was obtained with the 4-methylpentyl and the 2-methoxyethyl ALA esters.

Example 11

Gel Formulation

Hydroxyethyl cellulose (HEC) (150 mg, mw 720,000) is added to water (10 ml) and the mixture is stirred and heated to 70° C. The HEC dissolves and forms a gel. The mixture is cooled to 50° C. and 5-ALA benzyl ester HCl (300 mg) and benzyl alcohol (150 mg) are added to the gel with stirring. The mixture is stirred for 5 minutes and is filled into a 10 ml tube.

The gel contains 3% 5-ALA benzyl ester HCl and is ready for use.

Example 12

Cream Formulation

5-ALA isopropylbenzyl ester HCl (500 mg) is mixed into Ung. Merck (10 g) using a mortar and pestle. The resulting cream is filled into a vial.

The cream contains 5% 5-ALA isopropylbenzyl ester HCl and is ready for use.

Example 13

Clinical Use of Methyl ALA Ester

The objective of this clinical study was to investigate the efficacy and tolerability of photodynamic therapy (PDT) after topical application of methyl ALA ester for treatment of moderate inflammatory facial acne.

Thirty patients aged 15-28 years with moderate to severe acne were included in a blinded, prospective, randomised, placebo-controlled multicentre study. Each side of each patient's face was randomly assigned to treatment with cream containing 160 mg/g methyl aminolevulinate hydrochloride (sold under the tradename Metvix® by PhotoCure ASA, Norway) or placebo cream and covered with an adhesive occlusive dressing (Tegaderm®, 3M or Opsite®, Smith and Nephew). Nodular or cystic lesions were prepared using a cannula (1-2 mm) to facilitate cream penetration. After 3 hours, the cream was gently wiped off both sides of the face immediately before illumination with non-coherent red light using the Aktilite® CL 128 lamp (PhotoCure ASA, average wavelength 635 nm, light dose 37 J cm$^{-2}$). Illumination was then repeated for the other side of the face. The side of the face not receiving illumination was covered when the other side was illuminated.

A second treatment was given 2 weeks later. On each occasion, patients assessed the intensity of pain using a 10 cm visual analogue scale. Inflammatory and non-inflammatory acne lesions were counted at baseline (i.e. before the start of treatment) and 4 and 10 weeks after the last PDT treatment. The investigator assessed the global severity (see Table 2) of acne at baseline (seven patients had severe acne on at least one side of the face) and each study visit using a 6-point rating scale. Data were analysed on an intention-to-treat basis, including all 30 patients.

TABLE 2

| | | Investigator's global severity assessment |
|---|---|---|
| Rating | | Definition |
| 0 | Clear | Residual hyperpigmentation and erythema may be present |
| 1 | Almost Clear | A few scattered comedones and a few (less than five) small papules. |
| 2 | Mild | Easily recognisable; less than half the face is involved. Many comedones and many papules and pustules. |
| 3 | Moderate | More than half of the face is involved. Numerous comedones, papules and pustules. |
| 4 | Severe | Entire face is involved. Covered with comedones, numerous papules and pustules and few nodules and cysts. |
| 5 | Very Severe | Highly inflammatory acne covering the face; with nodules and cysts present. |

Figure 11:
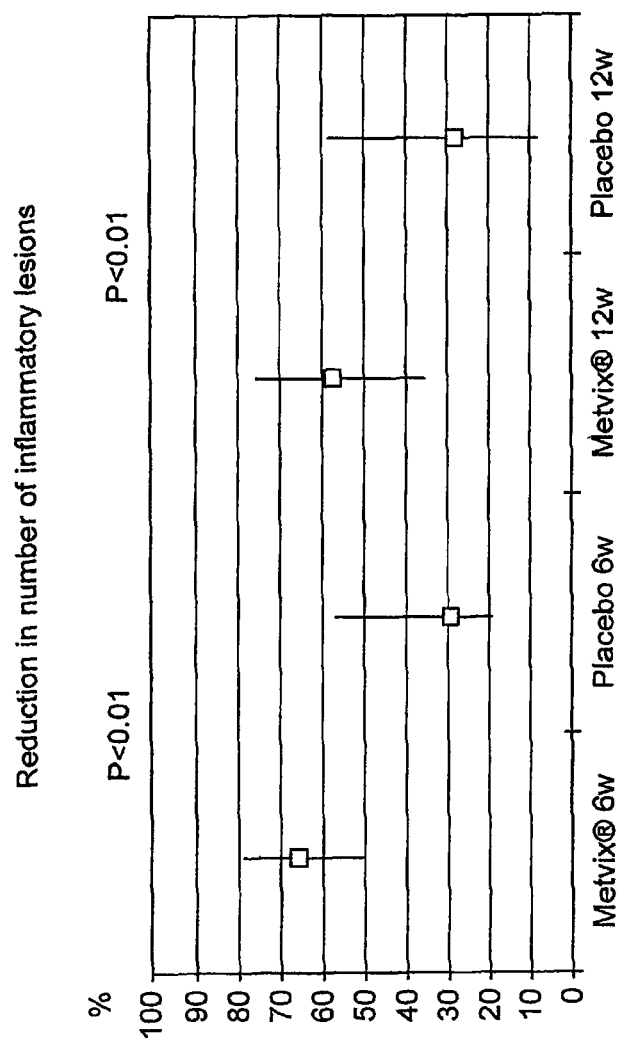
FIG. 11 shows the reduction of inflammatory lesions after treatment with Metvix® and PDT or placebo cream and PDT at 6 and 12 weeks after treatment.

The results of the study are shown in FIG. 11 wherein the results for each group are presented as the median (box) and the 50% percentile (bar) of all observations. This implies that for each group 25% of the observations are below and 25% are above the bar.

There was a statistically significant greater reduction in the total inflammatory lesion count with Metvix® PDT compared with placebo PDT at week 12 (median reduction 54% [95% CI 35% 64%] vs. 20% [95% CI 8%-50%], p=0.0006). Metvix® PDT was associated with more pain than placebo PDT, although its intensity varied across centres and was reduced with repeated treatment. Local adverse events were consistent with this treatment modality. It can be concluded that Metvix® PDT is effective in the treatment of moderate to severe inflammatory facial acne.

We claim:

1. A method of treating acne comprising administering to an area of skin affected by acne on a body an effective amount of a photosensitizer which is methyl 5-aminolevulinic acid (ALA) ester or a pharmaceutically acceptable salt thereof, and exposing the area to an effective amount of photoactivating light.

2. The method of claim 1, wherein the method comprises administering a pharmaceutically acceptable salt of methyl ALA ester.

3. The method of claim 2, wherein the method comprises administering the hydrochloride salt of methyl ALA ester.

4. The method of claim 3, wherein the hydrochloride salt of methyl ALA ester is applied in a composition at a concentration in the range of 0.02 to 25% w/w.

5. The method of claim 4, wherein the hydrochloride salt of methyl ALA ester is applied at a concentration in the range of about 5% w/w.

6. The method of claim 1, further comprising a waiting time period between administering the hydrochloride salt of methyl ALA ester and exposing the area to photoactivating light.

7. The method of claim 6, in which the waiting time period is from 1 to 3 hours.

8. The method of claim 7, in which the photoactivating light has a wavelength in the range of 300 to 800 nm.

9. The method of claim 8, in which the photoactivating light has a wavelength in the range of 580 to 740 nm.

10. The method of claim 9, in which the photoactivating light has an average wavelength of about 635 nm.

11. The method of claim 9, in which the photoactivating light is administered in a dose of 40 to 200 J/cm$^2$.

12. The method of claim 9, in which the photoactivating light is administered in a dose of 37 J/cm$^2$.

13. The method of claim 12, wherein the photoactivating light is provided by a LED light source.

14. The method of claim 1, wherein methyl ALA ester or a pharmaceutically acceptable salt thereof is administered in an oil-in-water emulsion cream formulation.

15. The method of claim 1, further comprising covering the administered methyl ALA ester or a pharmaceutically acceptable salt thereof with an occlusive dressing.

16. The method of claim 1, wherein the treated acne is acne vulgaris.

17. The method of claim 1, wherein the treated acne is moderate to severe acne.

18. The method of claim 17, wherein the treated acne is moderate acne.

19. The method of claim 17, wherein the treated acne is severe acne.

20. The method of claim 1, wherein the treated acne is characterized by inflammation.

21. The method of claim 1, wherein the treated acne is characterized by non-inflammatory lesions.

* * * * *